United States Patent
Daniel (10) Patent No.: US 9,724,197 B2
(45) Date of Patent: Aug. 8, 2017

(54) TOOL WITH A SUCTION FEATURE USEFUL FOR IMPLANTING A PENILE PROSTHETIC CYLINDER

(71) Applicant: Coloplast A/S, Humlebaek (DK)

(72) Inventor: Geoffrey A. Daniel, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 420 days.

(21) Appl. No.: 14/482,640

(22) Filed: Sep. 10, 2014

(65) Prior Publication Data

US 2016/0067045 A1    Mar. 10, 2016

(51) Int. Cl.
- A61F 5/00    (2006.01)
- A61F 2/26    (2006.01)
- A61F 5/41    (2006.01)

(52) U.S. Cl.
CPC .................. *A61F 2/26* (2013.01); *A61F 5/41* (2013.01); *A61F 2005/415* (2013.01)

(58) Field of Classification Search
CPC ........... A61F 2/26; A61F 5/41; A61B 17/3468
USPC ............... 600/38–41; 606/53–115, 119–128, 606/139–158, 205–211
See application file for complete search history.

(56) References Cited

U.S. PATENT DOCUMENTS

| | | |
|---|---|---|
| 3,704,712 A | 12/1972 | Giesy et al. |
| 3,893,456 A | 7/1975 | Small et al. |
| 4,049,002 A * | 9/1977 | Kletschka ............ A61B 17/2812 604/27 |
| 4,066,073 A | 1/1978 | Finney et al. |
| 4,201,202 A | 5/1980 | Finney et al. |
| 4,244,370 A | 1/1981 | Furlow et al. |
| 4,342,308 A | 8/1982 | Trick |
| 4,350,151 A | 9/1982 | Scott |
| 4,353,360 A | 10/1982 | Finney et al. |
| 4,369,771 A | 1/1983 | Trick |
| 4,399,812 A | 8/1983 | Whitehead |
| 4,449,520 A | 5/1984 | Palomar et al. |
| 4,558,693 A | 12/1985 | Lash et al. |
| 4,653,485 A | 3/1987 | Fishell |
| 4,726,360 A | 2/1988 | Trick et al. |
| 4,773,403 A | 9/1988 | Daly |
| 4,823,779 A | 4/1989 | Daly et al. |
| 4,829,990 A | 5/1989 | Thüroff et al. |
| 4,919,152 A * | 4/1990 | Ger ........................ A61B 17/29 128/898 |
| 4,995,380 A | 2/1991 | Maerzke et al. |

(Continued)

FOREIGN PATENT DOCUMENTS

| | | |
|---|---|---|
| CA | 1142049 A1 | 3/1983 |
| CN | 2737308 Y | 11/2005 |

(Continued)

*Primary Examiner* — John Lacyk
(74) *Attorney, Agent, or Firm* — Coloplast Corp., Coloplast A/S; Nick Baumann (57) ABSTRACT

A tool for implanting an inflatable penile prosthetic cylinder includes a pincher connected to a handle, a suction feature provided on the pincher, and an evacuation feature provided on the handle. The handle is operable to open the pincher a distance to receive the inflatable penile cylinder and operable to close the pincher against opposed sides of the inflatable penile cylinder. The suction feature is operable to couple the inflatable penile cylinder to the pincher. The evacuation feature is operable to provide suction to the suction feature.

12 Claims, 7 Drawing Sheets

(56) References Cited

U.S. PATENT DOCUMENTS

| | | |
|---|---|---|
| 5,167,611 A | 12/1992 | Cowan |
| 5,230,694 A | 7/1993 | Rosenblum |
| 5,344,388 A | 9/1994 | Maxwell et al. |
| 5,484,450 A | 1/1996 | Mohamed |
| 5,788,627 A | 8/1998 | Subrini |
| 5,828,757 A | 10/1998 | Michalsen et al. |
| 5,868,729 A | 2/1999 | Pelfrey |
| 5,895,424 A | 4/1999 | Steele, Sr. et al. |
| 5,899,849 A | 5/1999 | Elist |
| 5,968,067 A | 10/1999 | Mooreville et al. |
| 6,475,244 B2 | 11/2002 | Herweck et al. |
| 6,579,230 B2 | 6/2003 | Yachia et al. |
| 6,808,489 B2 | 10/2004 | George et al. |
| 6,808,490 B1 | 10/2004 | Ling et al. |
| 7,066,878 B2 | 6/2006 | Eid |
| 7,344,554 B2 | 3/2008 | Kuyava et al. |
| 7,407,482 B2 | 8/2008 | Kuyava |
| 7,914,578 B2 | 3/2011 | Vardi |
| 7,938,770 B2 | 5/2011 | Morningstar et al. |
| 7,959,556 B2 | 6/2011 | Morningstar |
| 8,002,692 B2 | 8/2011 | Morningstar et al. |
| 8,167,788 B2 | 5/2012 | Fogarty et al. |
| 8,192,352 B2 | 6/2012 | Morningstar et al. |
| 8,231,521 B2 | 7/2012 | Morningstar et al. |
| 8,360,959 B2 | 1/2013 | Morningstar |
| 8,403,825 B2 | 3/2013 | Morningstar |
| 8,419,612 B2 | 4/2013 | Daniel |
| 8,491,621 B2 | 7/2013 | Morningstar |
| 8,545,391 B2 | 10/2013 | Kuyava et al. |
| 8,636,645 B2 | 1/2014 | Daniel |
| 8,685,011 B2 | 4/2014 | Arcand |
| 8,702,589 B2 | 4/2014 | Kuyava |
| 2001/0005787 A1* | 6/2001 | Oz ................. A61B 17/064 606/142 |
| 2003/0220539 A1 | 11/2003 | George |
| 2004/0225182 A1 | 11/2004 | Eid |
| 2006/0225894 A1 | 10/2006 | Roll et al. |
| 2009/0048537 A1 | 2/2009 | Lydon et al. |
| 2010/0010530 A1 | 1/2010 | Rhee |
| 2010/0160722 A1 | 6/2010 | Kuyava et al. |
| 2011/0066226 A1 | 3/2011 | Bell et al. |
| 2011/0196271 A1 | 8/2011 | Forsell |
| 2012/0022323 A1 | 1/2012 | Forsell |
| 2012/0022324 A1 | 1/2012 | Forsell |
| 2012/0157763 A1 | 6/2012 | Darnell |
| 2012/0157764 A1 | 6/2012 | Borgaonkar et al. |
| 2013/0041212 A1 | 2/2013 | Chechik |
| 2013/0116655 A1 | 5/2013 | Bacino et al. |
| 2013/0226131 A1 | 8/2013 | Bacino et al. |

FOREIGN PATENT DOCUMENTS

| | | |
|---|---|---|
| CN | 201668855 U | 12/2010 |
| CN | 201668856 U | 12/2010 |
| CN | 201988037 U | 9/2011 |
| CN | 203001114 U | 6/2013 |
| DE | 3741879 A1 | 6/1988 |
| DE | 102010038975 A1 | 2/2012 |
| DE | 102010062072 A1 | 5/2012 |
| EP | 0682923 A1 | 11/1995 |
| ES | 1015196 U | 6/1991 |
| FR | 2532551 A1 | 3/1984 |
| IT | 223594 U | 7/1995 |
| IT | 1296983 B1 | 8/1999 |
| KR | 100596497 B1 | 7/2006 |
| KR | 100944789 B1 | 2/2010 |
| RU | 35594 | 1/2004 |
| RU | 58341 | 6/2006 |
| SU | 1084016 A1 | 4/1984 |
| WO | 8601398 A1 | 3/1986 |
| WO | 03071970 A1 | 9/2003 |
| WO | 2004045421 A1 | 6/2004 |
| WO | 2005072626 A1 | 8/2005 |
| WO | 2011023197 A1 | 3/2011 |
| WO | 2011035787 A1 | 3/2011 |
| WO | 2011072692 A1 | 6/2011 |
| WO | 2012069643 A1 | 5/2012 |
| WO | 2013049682 A1 | 4/2013 |
| WO | 2014052729 A2 | 4/2014 |
| WO | 2014099873 A1 | 6/2014 |

* cited by examiner

TOOL WITH A SUCTION FEATURE USEFUL FOR IMPLANTING A PENILE PROSTHETIC CYLINDER

BACKGROUND

An implanted penile prosthetic has proven useful in treating erectile dysfunction in men. The penile prosthetic includes two inflatable cylinders implanted in the penis, a pump implanted in the scrotum or other internal space, and a liquid holding reservoir implanted in the abdomen or other internal space.

In a typical implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic. Thereafter, a tool (e.g., a "Furlow" introducer) is inserted into each dilated corpora cavernosum to measure a length of the penis distally and proximally to determine a desired length of the cylinders. A cylinder of the appropriately selected length is secured to a suture, and the suture is secured to a needle (sometimes called a "Keith" needle) that is loaded into the Furlow introducer. The Furlow introducer delivers the needle through the dilated corpora cavernosum and out the glans penis. The needle is discarded and the suture is employed to tow the cylinder into place within the dilated corpora cavernosum.

The above-described procedure has proven effective when implanting penile prostheses. However, surgeons and users would both appreciate improved tools for implanting penile prosthetic cylinders.

SUMMARY

One aspect provides a tool for implanting an inflatable penile prosthetic cylinder. The tool includes a pincher connected to a handle, a suction feature provided on the pincher, and an evacuation feature provided on the handle. The handle is operable to open the pincher a distance to receive the inflatable penile cylinder and operable to close the pincher against opposed sides of the inflatable penile cylinder. The suction feature is operable to couple the inflatable penile cylinder to the pincher. The evacuation feature is operable to provide suction to the suction feature.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1A is an exploded side view of a prior art tool for implanting a cylinder into a penis as illustrated in cross-section in FIG. 1B.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other ("mixed and matched"), unless specifically noted otherwise.

End means endmost. A distal end is the furthest endmost location of a distal portion of a thing being described, whereas a proximal end is the nearest endmost location of a proximal portion of the thing being described. The portion next to or adjacent to an end is an end portion.

An implantable penile prosthetic system includes two cylinders implanted in the penis, a pump implanted in the scrotum or other internal space, and a liquid holding reservoir implanted in the abdomen or other internal space. The surgeon usually implants the reservoir last, after confirming that the tubing attached to the reservoir, pump, and cylinders is not leaking. The reservoir is filled with saline or another liquid at approximately atmospheric pressure. The pump is employed to transfer the liquid from the reservoir to the cylinders, and in so doing, the liquid in the cylinders is pressurized to create an erection. A flow path is provided to depressurize and return the liquid from the cylinders back to the reservoir.

Figures 1A, 1B:
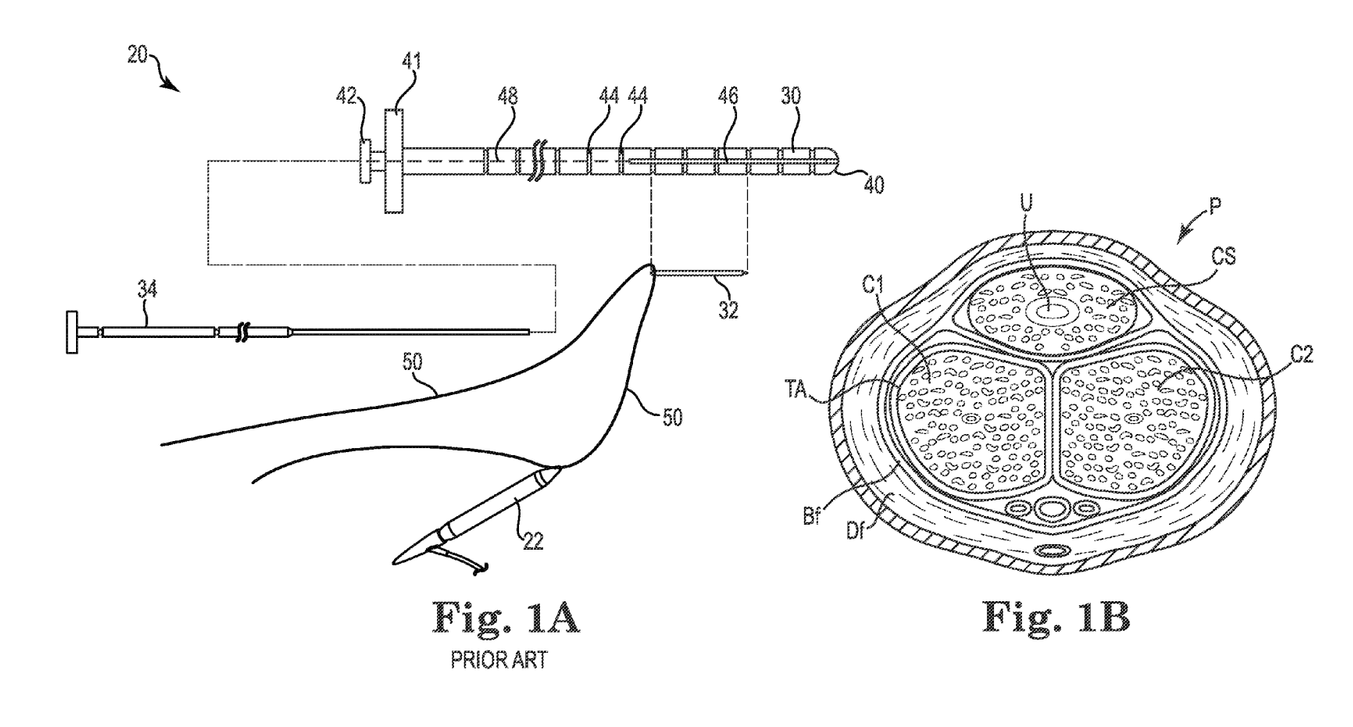

FIG. 1A is an exploded side view of a prior art tool 20 for implanting an inflatable cylinder 22 into a penis P illustrated in FIG. 1B. The inflatable cylinders 22 are fabricated to be pliant and comfortable when deflated and rigid and erect when inflated. The deflated cylinder 22 lacks column strength and will bend and twist and resist being pushed into the penis P. For this reason, a suture or strand is employed to pull the inflatable cylinder into place within the penis P.

The tool 20 includes a barrel 30, a needle 32 that is insertable into the barrel 30, and a plunger 34 that is insertable into the barrel 30 to push the needle 32 out of the barrel 30. One such needle 32 is a Keith needle.

The barrel 30 extends between a curved distal end 40 and a handle 41 provided at a proximal end 42. The barrel 30 has markings 44 applied on an external surface to indicate or measure a depth to which the barrel 30 has been inserted into the corpora cavernosum. The barrel 30 is provided with a slot 46 that is sized to receive the needle 32 and a lumen 48 sized to receive the needle 32 and the plunger 34.

The needle 32 is attached to a tow suture 50 that is coupled with the cylinder 22. The tow suture 50 is generally inserted through an eyelet of the needle 50 and a hole provided at a distal end of the cylinder 22.

The plunger 34 is insertable into the lumen 48 at the proximal end 42 of the barrel 30 and operates to push the needle 32 out of the lumen 48.

FIG. 1B is a cross-sectional view of the penis P oriented to access by the surgeon. The surgeon gains access to the corpora cavernosa though small incisions made through the fascia after the penis is reclined toward the abdomen, as illustrated in the cross-sectional view of FIG. 1B. In the view of FIG. 1B the penis P of the patient is reclined against the torso such that the urethra U, surrounded by corpus spongiosum CS tissue, is oriented upward.

In preparation for the implantation of the penile prosthesis, the groin area of the patient is shaved, cleaned and suitably prepped with a surgical solution prior to draping with a sterile drape as directed by the healthcare provider's procedures. A retraction device, such as a retractor sold under the trademark Lone Star and available from Lone Star Medical Products of Stafford, Tex., is placed around the penis P. A catheter is inserted into the urethra U from the distal end of the penis P into the bladder. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum.

In the transverse scrotal approach the surgeon forms a 2-3 cm transverse incision through the subcutaneous tissue of the median raphe of the upper scrotum and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed to allow the surgeon to access to the corpora cavernosa C1 and C2.

Each corpora cavernosum C1, C2 is dilated with an appropriate dilation tool to form a recess in the penis P that is sized to receive one of the two cylinders 22. The barrel 30 of the tool 20 is inserted into each dilated corpora cavernosum C1, C2 to measure the length of the corpora prior to selecting an appropriately sized cylinder 22. The barrel 30 is removed from the penis P. The suture 50 is inserted through the distal, leading end of the cylinder 22 and the needle 32. The needle 32 is loaded into the barrel 30 through the slot 46 and the plunger 34 is inserted into the lumen 48 via the proximal end 42 of the barrel 30. The barrel 30 is inserted into the dilated corpora cavernosum and the plunger 34 is pushed into the lumen 48 to push the needle 32 out of the barrel 30 and through the glans penis. The surgeon captures the needle 32, disengages the needle 32 from the tow suture 50, and pulls on the tow suture 50 to draw the cylinder 22 into the dilated corpora cavernosum. The tow suture 50 is disengaged from the cylinder, which is now implanted within the corpora cavernosum C1 or C2.

Pushing the needle 32 through the glans penis can cause bleeding from the head of the penis, which while harmless, can be alarming to the patient. Surgeons have expressed a desire to avoid the use of the needle 32.

As noted above, the suture 50 is inserted through the distal, leading end of the cylinder 22. The distal end of the cylinder 22 is oftentimes structurally reinforced to accommodate the hole that the suture 50 is passed through. The reinforced end of the cylinder can be felt by some patients who perceive it as a hard and unnatural, undesirable pointed projection.

Embodiments provide a tool for implanting an inflatable penile prosthetic cylinder into a penis, where the tool does away with the handling and the use of a Keith needle. The tool is useful for positively engaging with the cylinder and pushing the prosthetic cylinder into the opening formed in the penis. The tool operates to secure the cylinder in the distal region of the corpora cavernosum with access into and out of the penis through a single incision/opening. The tool may be fabricated from plastic or metal and can be provided in both disposable and reusable forms.

Figure 2:
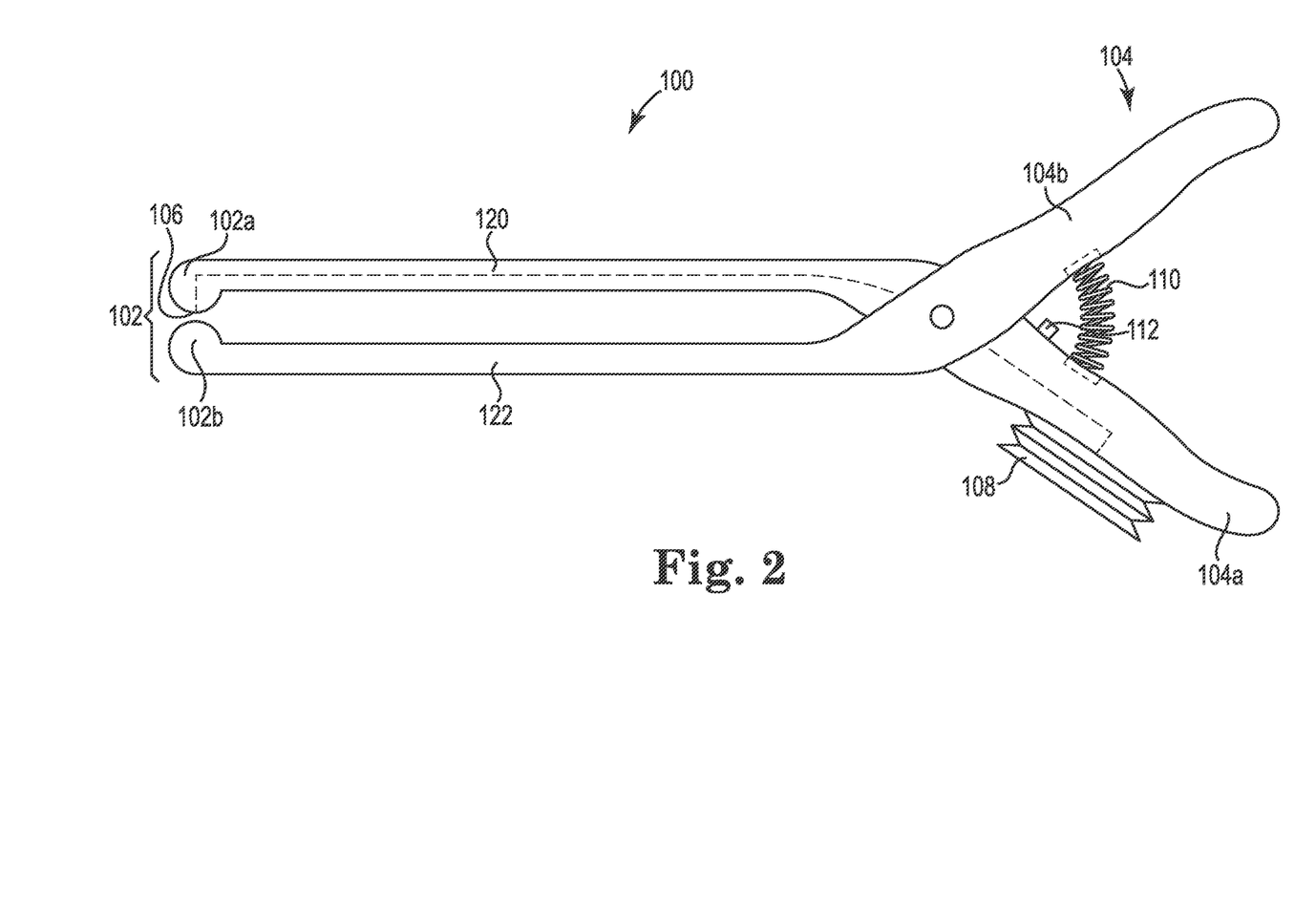
FIG. 2 is a side view of one embodiment of a tool for implanting an inflatable penile prosthetic cylinder.

FIG. 2 is a side view of one embodiment of a tool 100 for implanting an inflatable penile prosthetic cylinder.

The tool 100 includes a pincher 102 connected to a handle 104, a suction feature 106 provided on the pincher 102, and an evacuation feature 108 provided on handle 104. The handle 104 is operable to open the pincher 102 a distance that is sufficient to receive an inflatable penile cylinder. In one embodiment, a bias member 110 is connected to the handle 104. The bias member 110 is provided to bias and retain the pincher 102 into a closed position. The suction feature 106 is operable to create a sufficient vacuum to hold the inflatable penile cylinder in the pincher 102. The evacuation feature 108 is operable to provide suction or a vacuum to the suction feature 106, which in the presence of inflatable cylinder, draws the cylinder into engagement with the pincher 102. In one embodiment, the tool 100 includes a suction release feature 112 that operates to release the suction provided at the pincher 102.

The suction feature 106 is acceptably provided as a vacuum port and the evacuation feature 108 is acceptably provided as a bellows that communicates with the vacuum port. Compression and expansion of the bellows draws air through the vacuum port and ejects the air out of the bellows. A suitable check valve assembly, described below, is provided to allow the vacuum port to establish a vacuum as the air is removed through the vacuum port.

In one embodiment, the pincher 102 includes opposed first and second pinch surfaces 102a, 102b. The tool 100 includes a first blade 120 connected between the first pinch surface 102a and a first handle portion 104a, and a second blade 122 connected between the second pinch surface 102b and a second handle portion 104b. In the illustration of FIG. 2, the first pinch surface 102a and the second pinch surface 102b are both located on a proximal portion of a respective one of the blades 120, 122.

In one embodiment, the tool 100 includes one suction feature 106 provided on the first pinch surface 102a. In another embodiment, the tool 100 includes a suction feature provided on each of the first and second pinch surfaces 102a, 102b.

The suction feature(s) 106 are illustrated located on the pincher(s) 102, although it is acceptable to locate the suction feature(s) elsewhere on one or both of the blades 120, 122.

The evacuation feature 108 is illustrated located on the handle 104, although it is acceptable to locate the evacuation feature elsewhere on the tool 100.

The tool 100 is useful for implanting an inflatable penile cylinder into a dilated corpora cavernosum. The surgeon is instructed to grasp the tool 100 by the handle 104, squeeze the handle 104 to open the pincher 102, and place an inflatable cylinder between the blades 120, 122. The handle 104 is released, and in cooperation with the bias feature 110, the inflatable cylinder is captured between the pincher 102. The evacuation feature 108 is operated to provide suction at the suction feature 106 between the pincher 102 to ensure that the inflatable cylinder is secured between the pincher 102. The inflatable cylinder secured by the tool 100 is inserted into the corpora cavernosum until a distal end of the cylinder is seated in the distal end of the corpora cavernosum. The suction release feature 112 is activated to release the suction at the suction feature 106, which releases the inflatable cylinder from the pincher 102. Thereafter, the tool 100 is removed from the corpora cavernosum leaving the cylinder in place within the penis.

The tool 100 is suitable fabricated from plastic or metal and embodiments include disposable single-use and reusable variations of the tool 100.

Figures 3A, 3B:
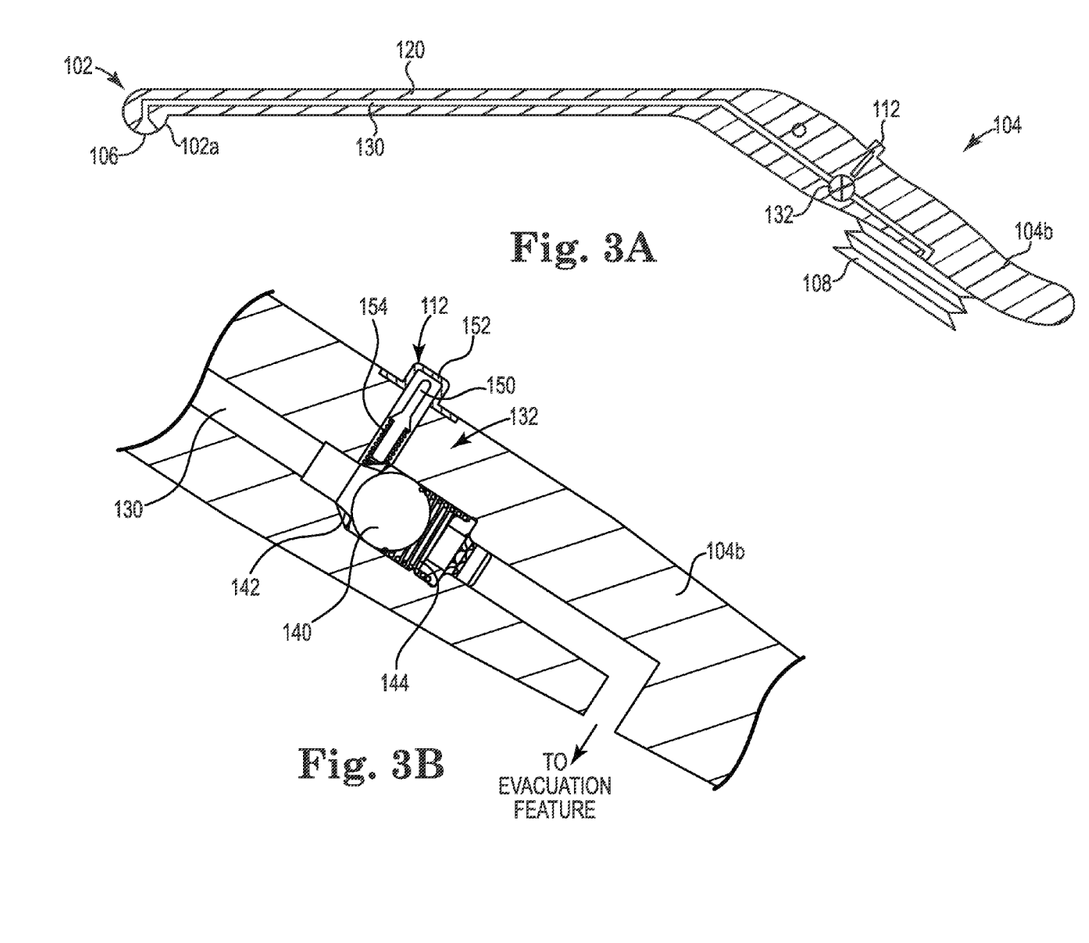
FIG. 3A is a cross-sectional view of one blade of the tool illustrated in FIG. 2.
FIG. 3B is a cross-sectional view of a valve assembly of the blade illustrated in FIG. 3A.

FIG. 3A is a cross-sectional view of a portion of the tool illustrated in FIG. 2. The first blade 120 extends between the first pinch surface 102a and the second handle portion 104b. The suction feature 106 is provided on the first pinch surface 102a and communicates with the evacuation feature 108 through a channel 130. The evacuation feature 108 draws air through the channel 130 to provide a vacuum at the suction feature 106. The direction of the air flow during suction is from the suction feature 106 to the evacuation feature 108. In one embodiment, a valve assembly 132 is provided to prevent the suctioned air from undesirably flowing in a direction from the evacuation feature 108 back to the suction feature 106.

FIG. 3B is a cross-sectional view of the second handle portion 104b and the valve assembly 132. With reference to FIG. 3A, the valve assembly 132 includes a valve 140 biased into engagement with a seat 142 of the channel 130 by a spring 144. In one embodiment, the valve assembly 132 is a check valve or a one-way valve that prevents the flow of air from the evacuation feature 108 back to the suction feature 106. Other suitable valve assemblies include diaphragm valve assemblies.

The evacuation feature 108 pulls air through the channel 130 as indicated by the "to evacuation feature" marking. The evacuation feature 108 includes an ejection port that allows the air drawn through the channel 130 to be ejected out from the evacuation feature 108, which assists in creating the vacuum at the suction feature 106. The ejection port desirably ejects air rearward away from the patient.

The evacuation feature 108 provides a low pressure region downstream from the valve assembly 132, which results in the valve 140 moving off of the seat 142 to allow air to flow through the channel 130 from the suction feature 106 to the evacuation feature 108. The spring 144 biases the valve 140 onto the seat 142 to prevent the air from flowing back upstream to the suction feature 106. In this manner, a vacuum is created at the suction feature 106.

The suction provided at the suction feature 106 provides a retention force that retains the inflatable penile cylinder in the pincher 102. It is desirable to break the seal of the vacuum after inflatable penile cylinder is placed in the corpora cavernosum. The suction release feature 112 is operable to displace the valve 140 away from the seat 142 to break the seal of the vacuum at 106. In one embodiment, the suction release feature 112 includes a pin 150 that is retained within the body of the handle portion 104b in a deformable or movable housing feature 152. For example, in one embodiment the pin 150 is biased by a spring 154 that is configured to move in response to pressure applied to the deformable housing feature 152. One acceptable deformable housing feature 152 is a pliant polymer cap formed over the pin 150. Movement of the pin 150 into the second handle portion 104b presses the pin 150 against the seat 142 to deform/displace the seat 142, which moves the valve 140, to allow the air to flow upstream and release the vacuum at the suction feature 106.

Figure 4:
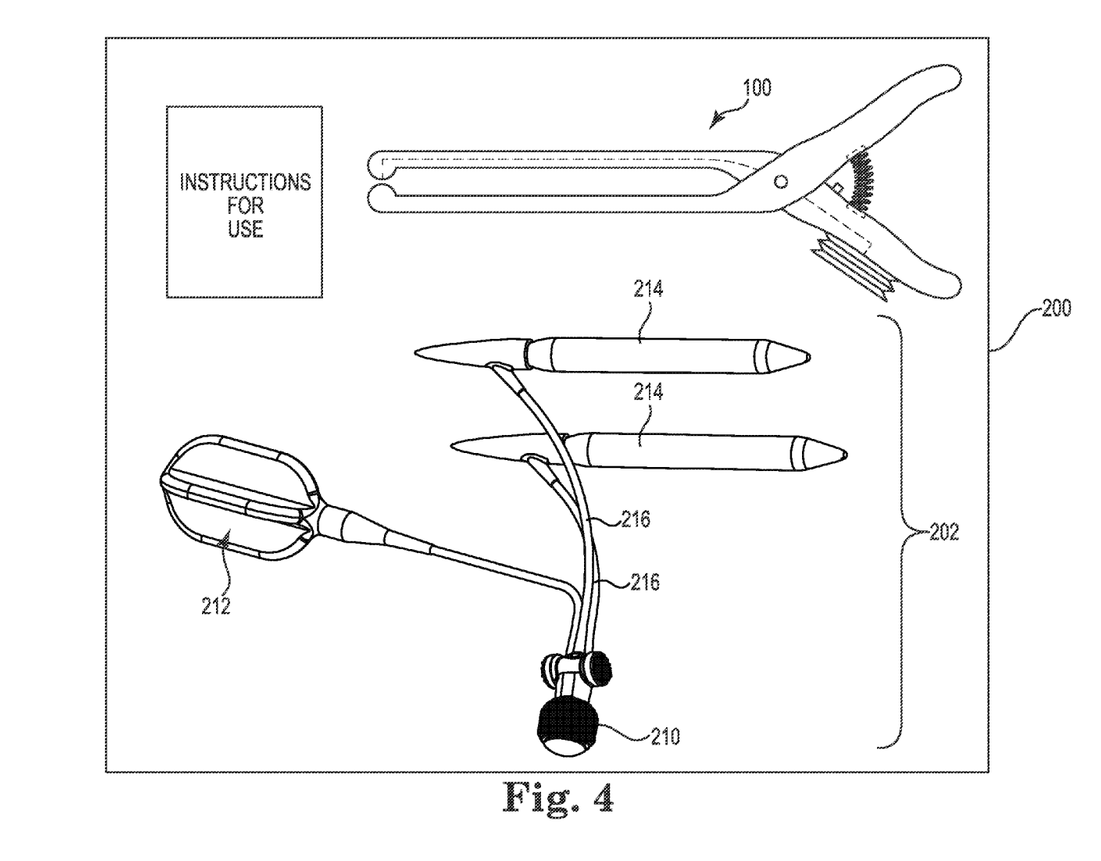
FIG. 4 is a schematic view of a kit of parts including the tool illustrated in FIG. 2.

FIG. 4 is a schematic view of a kit of parts 200. The kit of parts includes the tool 100, an implantable penile prosthetic system 202, and instructions for use of the tool 100. The implantable penile prosthetic system 202 includes a pump 210 connectable between a reservoir 212 and two inflatable penile prosthetic cylinders 214. The implantable penile prosthetic system 202 is shown in an assembled state for simplicity of discussion with the cylinders 214 connected to the pump 210 by tubing 216. Typically, the cylinders 214 are connected to the pump 210 after implantation. The pump 210 operates to move liquid from the reservoir 212 into the inflatable cylinders 214. The inflated cylinders 214, when implanted, provide the penis with an erection. The inflatable cylinders 214 can be deflated by evacuating the air and the liquid from the cylinders, which collapses the cylinders 214 into a flat, pancake shape.

Figure 5:
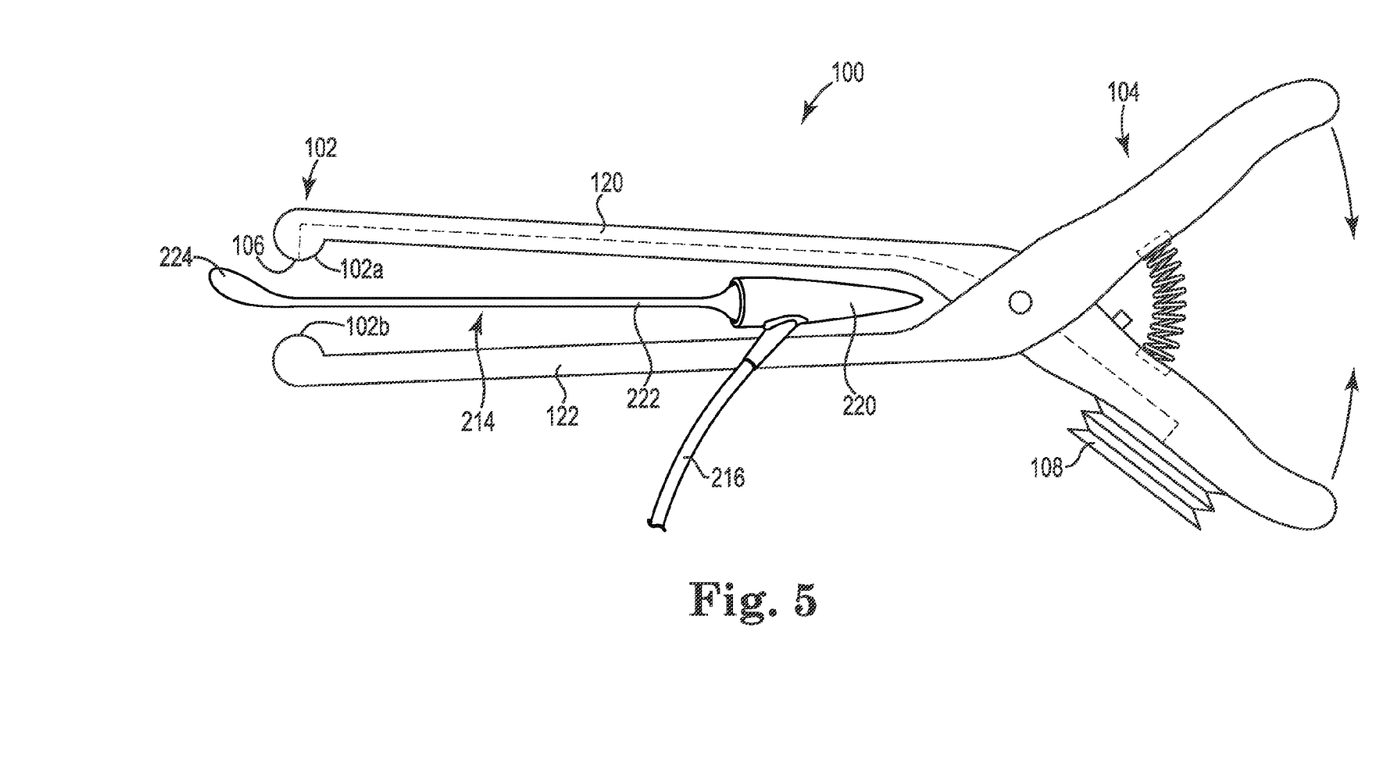
FIG. 5 is a side view of the tool illustrated in FIG. 2 with opposed blades in an open position.

FIG. 5 is a side view of the cylinder 214 loaded into the tool 100. The handle 104 has been squeezed against the resistance of the bias member 110 to open the blades 120, 122 a suitable distance to receive the cylinder 214.

The cylinder 214 includes a conically-shaped proximal tip 220 connected to a soft inflatable bladder 222 that terminates in a distal end 224. The inflatable bladder 222 can be deflated by applying a vacuum to the tubing 216. When deflated, the inflatable bladder 222 of the cylinder 214 collapses into a pancake-like shape. The distal end 224 of the cylinder 214 can have a thicker side wall that offers more mass at the leading end of the inflatable bladder 222. The pincher 102 is provided to grasp the inflatable bladder 222 proximal of the distal end 224.

Figure 6:
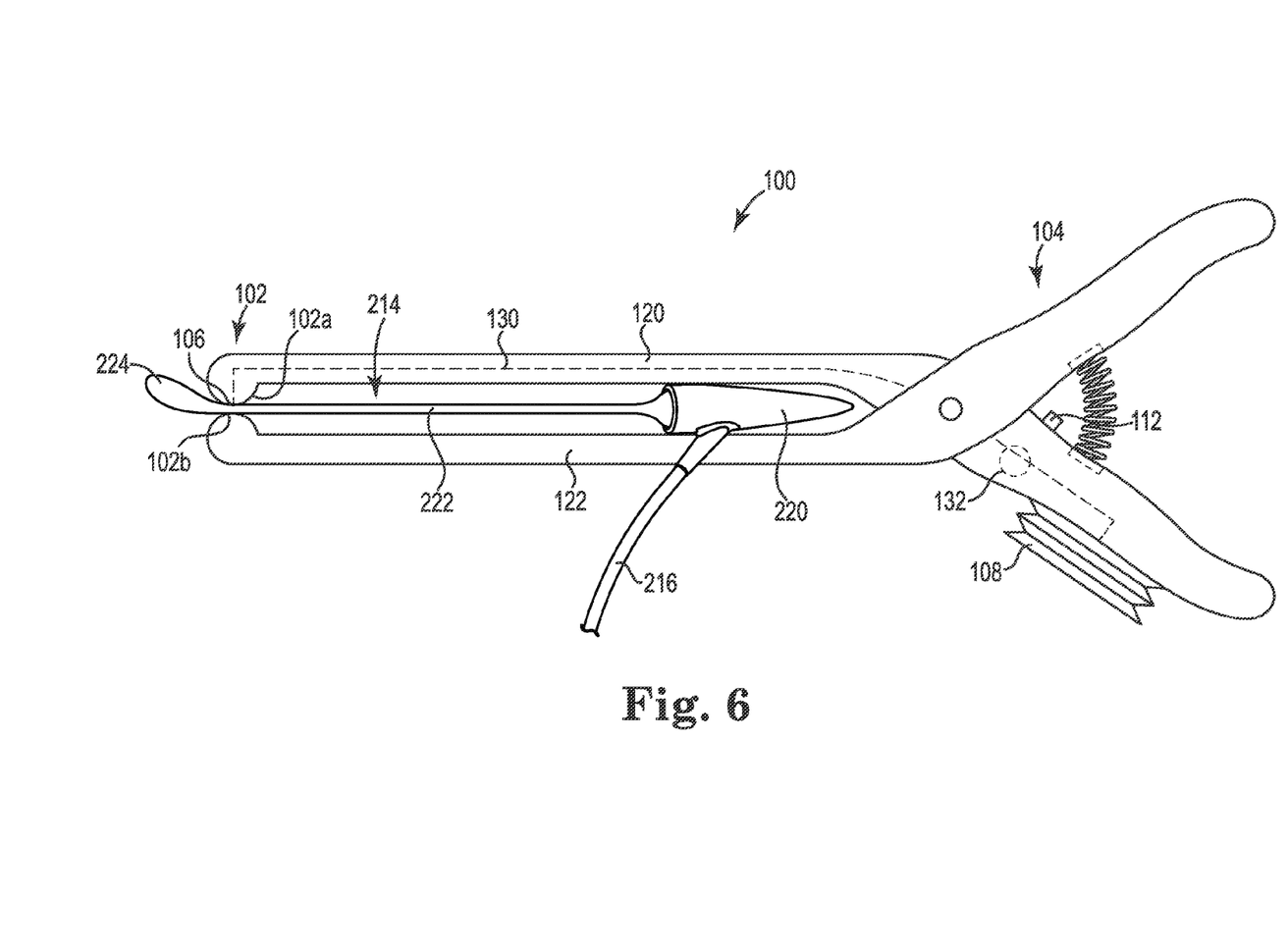
FIG. 6 is a side view of an inflatable penile prosthetic cylinder captured between the opposed blades illustrated in FIG. 5.

FIG. 6 is a side view of the cylinder 214 secured within the pincher 102. The bias feature 110 has pushed the handle 104 closed to capture the inflatable bladder 222 between the first pinch surface 102a and the second pinch surface 102b. The distal end 224 of the cylinder 214 projects a short distance beyond the pincher 102, which can be helpful in parting tissue or guiding the cylinder 214 when inserting the tool 100 and the cylinder 214 into a dilated corpora cavernosum. Suction is applied to the suction feature 106 by activating the evacuation feature 108 to draw air from the suction feature 106 through the channel 130 and through the valve assembly 132. The suction applied by the suction feature 106 at the pincher 102 operates to retain the deflated cylinder 214 even in the case where the handle 104 may be displaced and undesirably open the blades 120, 122.

The pincher 102 and the blades 120, 122, with the cylinder 214 captured between the blades, are sized for insertion into a dilated corpora cavernosum. The tool 100 with the deflated cylinder 214 captured within the pincher 102 is inserted into a dilated corpora cavernosum until the distal end 224 of the cylinder 214 is proximate the glans penis. Thereafter, the suction applied to the suction feature 106 is removed by activating the suction release feature 112 that allows the pressure in the channel 130 to return to atmospheric pressure. The deflated cylinder 214 is free to move away from the pincher 102. The inflatable bladder 122 can be provided with a lubricious surface or coating to aid in placing the cylinder 214 into the penis. The pincher 102, absent the suction, easily glides over the inflatable bladder 222 to allow the tool 100 to be removed from the penis may be in the cylinder 214 in place.

Figure 7:
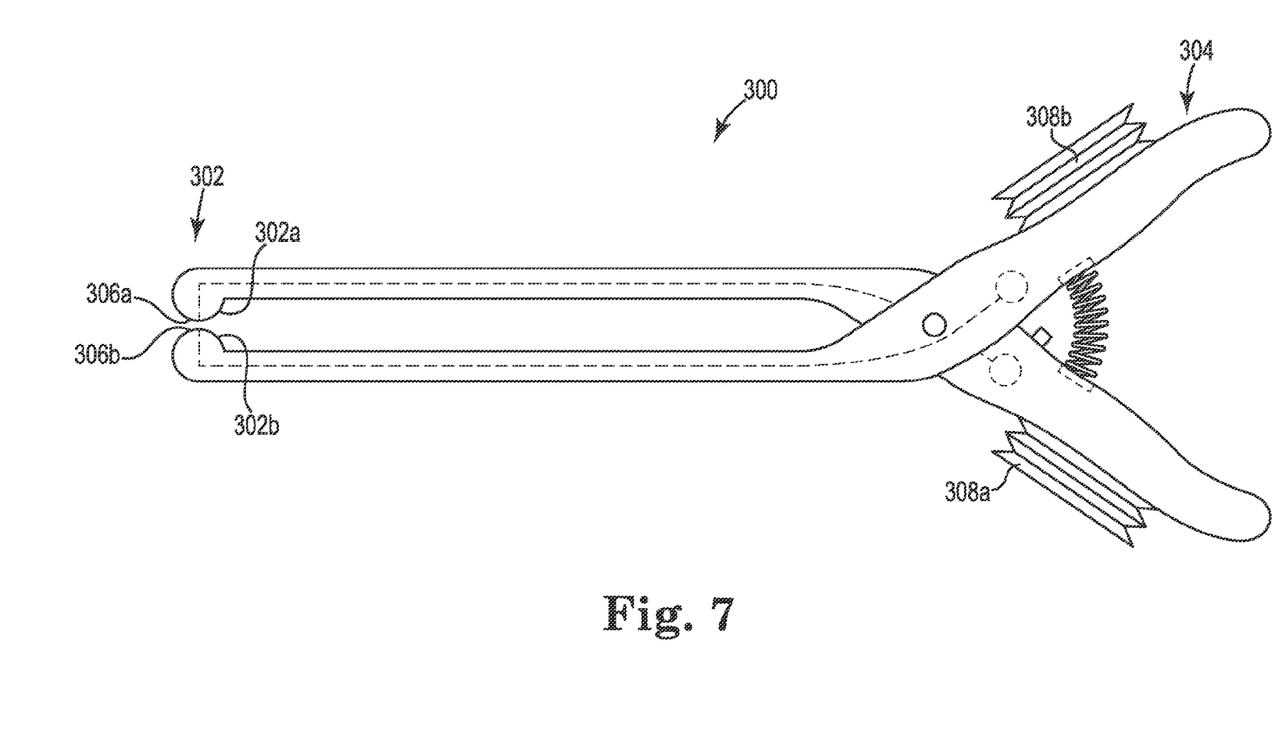
FIG. 7 is a side view of one embodiment of a tool for implanting an inflatable penile prosthetic cylinder.

FIG. 7 is a side view of one embodiment of a tool 300. The tool 300 is provided with a pincher 302 on an end opposite from a handle 304, where each opposed pinch surface 302a, 302b is provided with a respective suction feature 306a, 306b. Each suction feature 306a, 306b communicates with a respective evacuation feature 308a, 308b in a manner similar to that described above for suction feature 106 and evacuation feature 108.

Embodiments provide an improved tool for implanting a prosthetic cylinder of an implantable device useful for treating erectile dysfunction. The tool described in this application obviates the use of a Keith needle and does away with perforating the glans penis when implanting a prosthetic cylinder.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A tool for implanting an inflatable penile cylinder, the tool comprising:
   a pincher connected to a handle, the handle operable to open the pincher a distance to adapt the pincher to receive the inflatable penile cylinder and operable to close the pincher to adapt the pincher to close against opposed sides of the inflatable penile cylinder;
   a suction feature provided on the pincher, the suction feature operable to couple the inflatable penile cylinder to the pincher; and
   an evacuation feature provided on the handle, the evacuation feature operable to provide suction to the suction feature;
   wherein the suction feature is a vacuum port and the evacuation feature is a bellows communicating with the vacuum port.

2. The tool of claim 1, wherein the pincher includes a first pinch surface located on a proximal portion of a first blade of the tool and an opposed second pinch surface located on a proximal portion of a second blade of the tool, with the first blade connected to a first handle portion of the handle and the second blade connected to a second handle portion of the handle.

3. The tool of claim 1, wherein the pincher includes opposed first and second pinch surfaces and one of the opposed first and second pinch surfaces is provided with the suction feature.

4. The tool of claim 1, wherein the pincher includes opposed first and second pinch surfaces, with each of the opposed first and second pinch surfaces is provided with the suction feature.

5. The tool of claim 1, further comprising:
   a valve assembly located between the suction feature and the evacuation feature.

6. The tool of claim 5, further comprising:
   a suction release feature connected to the handle and communicating with the valve assembly, the suction release feature operable to release the suction provided to the suction feature.

7. The tool of claim 1, further comprising:
   a bias member connected to the handle, the bias member provided to bias the pincher into a closed pincher position.

8. A tool for implanting an inflatable penile cylinder into a corpora cavernosum, the tool comprising:
   a pincher connected to a handle, the handle operable to open the pincher a distance to adapt the pincher to receive the inflatable penile cylinder and operable to close the pincher;
   a vacuum port provided on the pincher;
   a bellows provided on the handle with the bellows communicating with the vacuum port, where the bellows is operable to suction the inflatable penile cylinder into contact with the pincher; and
   a channel formed in the handle, the channel communicating between the suction feature and the evacuation feature.

9. The tool of claim 8, further comprising:
   a valve assembly located in the channel between the suction feature and the evacuation feature.

10. The tool of claim 9, wherein the valve assembly is a one-way valve that prevents air flow from the evacuation feature to the suction feature.

11. The tool of claim 9, further comprising:
    a suction release feature connected to the handle and communicating with the valve assembly.

12. A kit of parts comprising:
    an implantable penile prosthetic system including a pump attachable between a reservoir and two inflatable penile prosthetic cylinders; and
    a tool provided to implant each of the two inflatable penile prosthetic cylinders into a penis, the tool including: a pincher connected to a handle, the handle operable to open the pincher a distance to receive each one of the two inflatable penile prosthetic cylinders; a suction feature provided on the pincher; an evacuation feature provided to suction each one of the two inflatable penile prosthetic cylinders into contact with the pincher; a channel formed to communicate between the suction feature and the evacuation feature; and instructions for use of the tool.

* * * * *